US008489172B2

(12) United States Patent
Gelbart et al.

(10) Patent No.: US 8,489,172 B2
(45) Date of Patent: Jul. 16, 2013

(54) LIPOSUCTION SYSTEM

(75) Inventors: Daniel Gelbart, Vancouver (CA); Samuel Victor Lichtenstein, Vancouver (CA)

(73) Assignee: Kardium Inc., Richmond (CA)

( * ) Notice: Subject to any disclaimer, the term of this patent is extended or adjusted under 35 U.S.C. 154(b) by 1218 days.

(21) Appl. No.: 12/010,458

(22) Filed: Jan. 25, 2008

(65) Prior Publication Data
US 2009/0192441 A1    Jul. 30, 2009

(51) Int. Cl.
*A61B 5/05* (2006.01)
(52) U.S. Cl.
USPC ............... 600/407; 601/2; 604/20; 604/22; 604/542
(58) Field of Classification Search
USPC ........... 600/407, 547, 442; 601/2–4; 604/22, 604/35, 131; 606/45, 46, 115, 159; 607/2, 607/8, 96–99, 101, 116
See application file for complete search history.

(56) References Cited

U.S. PATENT DOCUMENTS

| | | | |
|---|---|---|---|
| 4,114,202 A | 9/1978 | Roy et al. | 3/1.5 |
| 4,164,046 A | 8/1979 | Cooley | 3/1.5 |
| 4,225,148 A | 9/1980 | Andersson | 280/95 R |
| 4,240,441 A | 12/1980 | Khalil | 128/692 |
| 4,263,680 A | 4/1981 | Reul et al. | 3/1.5 |
| 4,273,128 A | 6/1981 | Lary | 128/305 |
| 4,411,266 A | 10/1983 | Cosman | 128/303.18 |
| 4,490,859 A | 1/1985 | Black et al. | 3/1.5 |
| 4,543,090 A | 9/1985 | McCoy | 604/95 |
| 4,770,187 A | 9/1988 | Lash et al. | |
| 4,794,912 A | 1/1989 | Lia | 128/4 |
| 4,850,957 A | 7/1989 | Summers | 604/22 |
| 4,887,613 A | 12/1989 | Farr et al. | 606/159 |
| 4,890,602 A | 1/1990 | Hake | 128/4 |
| 4,890,612 A | 1/1990 | Kensey | 606/213 |
| 4,893,613 A | 1/1990 | Hake | 128/4 |
| 4,895,166 A | 1/1990 | Farr et al. | 128/751 |

(Continued)

FOREIGN PATENT DOCUMENTS

| | | |
|---|---|---|
| EP | 0723467 | 4/2002 |
| WO | 95/10320 | 4/1995 |

(Continued)

OTHER PUBLICATIONS

Gabriel, Gabriel & Corthout: "The Dielectric Properties of Biological Tissues: Literature Survey" Phys. Med. Biol. 41, 1996, 2231-2249 (Printed in the U.K.).

(Continued)

*Primary Examiner* — Unsu Jung
*Assistant Examiner* — Daniel Huntley
(74) *Attorney, Agent, or Firm* — Seed IP Law Group PLLC

(57) ABSTRACT

A surgical tool such as a liposuction cannula is equipped with a sensor at the tool tip. The sensor continuously analyzes the type of tissue in contact with the tip based on the electrical properties of the tissue. When encountering a tissue type that should not be disturbed, the action of the surgical tool is stopped automatically. When used for liposuction, the cannula is mechanically decoupled from the handle when the wrong type of tissue is detected thus minimizing the inertia of the part that needs to be stopped. Besides electrical sensing, other sensors, such as mechanical or ultrasonic, can be used at the tip of the surgical tool or cannula to differentiate between tissue types.

23 Claims, 4 Drawing Sheets

U.S. PATENT DOCUMENTS

| | | | |
|---|---|---|---|
| 4,921,499 A | 5/1990 | Hoffman et al. | 623/16 |
| 4,942,788 A | 7/1990 | Farr et al. | 76/115 |
| 4,979,514 A | 12/1990 | Sekii et al. | 128/713 |
| 4,998,933 A | 3/1991 | Eggers et al. | 606/41 |
| 5,026,384 A | 6/1991 | Farr et al. | 606/159 |
| 5,047,047 A | 9/1991 | Yoon | 606/216 |
| 5,122,137 A | 6/1992 | Lennox | 606/40 |
| 5,127,902 A | 7/1992 | Fischell | 604/22 |
| 5,156,151 A | 10/1992 | Imran | 128/642 |
| 5,174,299 A | 12/1992 | Nelson | 128/692 |
| 5,176,693 A | 1/1993 | Pannek, Jr. | 606/159 |
| 5,178,620 A | 1/1993 | Eggers et al. | 606/41 |
| 5,192,291 A | 3/1993 | Pannek, Jr. | 606/159 |
| 5,201,316 A | 4/1993 | Pomeranz et al. | 128/662.06 |
| 5,228,442 A | 7/1993 | Imran | 128/642 |
| 5,242,386 A | 9/1993 | Holzer | |
| 5,279,299 A | 1/1994 | Imran | 128/642 |
| 5,293,869 A | 3/1994 | Edwards et al. | 128/642 |
| 5,312,435 A | 5/1994 | Nash et al. | 606/213 |
| 5,317,952 A | 6/1994 | Immega | 91/418 |
| 5,341,807 A | 8/1994 | Nardella | 128/642 |
| 5,366,443 A | 11/1994 | Eggers et al. | 604/114 |
| 5,379,773 A | 1/1995 | Hornsby | |
| 5,419,767 A | 5/1995 | Eggers et al. | 604/114 |
| 5,450,860 A | 9/1995 | O'Connor | 128/898 |
| 5,478,353 A | 12/1995 | Yoon | 606/216 |
| 5,496,267 A | 3/1996 | Drasler et al. | 604/22 |
| 5,531,760 A | 7/1996 | Alwafaie | 606/216 |
| 5,557,967 A | 9/1996 | Renger | 73/204.24 |
| 5,593,424 A | 1/1997 | Northrup III | 606/232 |
| 5,598,848 A | 2/1997 | Swanson et al. | 128/696 |
| 5,662,587 A | 9/1997 | Grundfest et al. | 600/114 |
| 5,681,308 A | 10/1997 | Edwards et al. | 606/41 |
| 5,681,336 A | 10/1997 | Clement et al. | 606/159 |
| 5,687,723 A | 11/1997 | Avitall | 128/642 |
| 5,697,285 A | 12/1997 | Nappi et al. | 91/519 |
| 5,713,896 A | 2/1998 | Nardella | |
| 5,716,397 A | 2/1998 | Myers | 623/2 |
| 5,720,726 A | 2/1998 | Marcadis et al. | 604/96 |
| 5,728,114 A | 3/1998 | Evans et al. | 606/148 |
| 5,730,127 A | 3/1998 | Avitall | 128/642 |
| 5,762,066 A * | 6/1998 | Law et al. | 600/439 |
| 5,769,846 A | 6/1998 | Edwards et al. | 606/41 |
| 5,782,239 A | 7/1998 | Webster, Jr. | 128/642 |
| 5,782,879 A | 7/1998 | Rosborough et al. | 607/6 |
| 5,800,495 A | 9/1998 | Machek et al. | 607/116 |
| 5,824,066 A | 10/1998 | Gross | 623/2 |
| 5,836,990 A | 11/1998 | Li | 607/28 |
| 5,876,343 A | 3/1999 | Teo | 600/443 |
| 5,881,727 A | 3/1999 | Edwards | 128/642 |
| 5,891,136 A | 4/1999 | McGee et al. | 606/41 |
| 5,904,711 A | 5/1999 | Flom et al. | 607/129 |
| 5,919,207 A | 7/1999 | Taheri | 606/219 |
| 5,921,924 A | 7/1999 | Avitall | 600/374 |
| 5,935,075 A | 8/1999 | Casscells et al. | 600/474 |
| 5,935,079 A | 8/1999 | Swanson et al. | 600/509 |
| 5,961,440 A | 10/1999 | Schweich, Jr. et al. | 600/16 |
| 5,984,950 A | 11/1999 | Cragg et al. | 606/216 |
| 6,001,069 A | 12/1999 | Tachibana et al. | 601/2 |
| 6,104,944 A | 8/2000 | Martinelli | 600/424 |
| 6,138,043 A | 10/2000 | Avitall | 600/377 |
| 6,142,993 A | 11/2000 | Whayne et al. | 606/41 |
| 6,156,046 A | 12/2000 | Passafaro et al. | 606/159 |
| 6,210,432 B1 | 4/2001 | Solem et al. | 623/1.15 |
| 6,217,573 B1 | 4/2001 | Webster | 606/41 |
| 6,241,747 B1 | 6/2001 | Ruff | 606/216 |
| 6,248,124 B1 | 6/2001 | Pedros et al. | 606/213 |
| 6,258,258 B1 | 7/2001 | Sartori et al. | 208/263 |
| 6,266,550 B1 | 7/2001 | Selmon et al. | 600/407 |
| 6,304,769 B1 | 10/2001 | Arenson et al. | 600/424 |
| 6,306,135 B1 | 10/2001 | Ellman et al. | 606/45 |
| 6,308,091 B1 | 10/2001 | Avitall | 600/374 |
| 6,346,105 B1 | 2/2002 | Tu et al. | 606/41 |
| 6,358,258 B1 | 3/2002 | Arcia et al. | 606/139 |
| 6,383,151 B1 | 5/2002 | Diederich et al. | 601/2 |
| 6,389,311 B1 | 5/2002 | Whayne et al. | 600/523 |
| 6,391,048 B1 | 5/2002 | Ginn et al. | 606/213 |
| 6,391,054 B2 | 5/2002 | Carpentier et al. | 623/2.37 |
| 6,402,781 B1 | 6/2002 | Langberg et al. | 623/2.36 |
| 6,436,052 B1 | 8/2002 | Nikolic et al. | 600/529 |
| 6,475,223 B1 | 11/2002 | Werp et al. | 606/108 |
| 6,485,409 B1 | 11/2002 | Voloshin et al. | 600/115 |
| 6,485,489 B2 | 11/2002 | Teirstein et al. | 606/41 |
| 6,506,210 B1 | 1/2003 | Kanner | 606/213 |
| 6,514,249 B1 | 2/2003 | Maguire et al. | 606/41 |
| 6,529,756 B1 | 3/2003 | Phan et al. | 600/374 |
| 6,537,198 B1 | 3/2003 | Vidlund et al. | 600/16 |
| 6,537,314 B2 | 3/2003 | Langberg et al. | 623/2.36 |
| 6,540,670 B1 | 4/2003 | Hirata et al. | 600/152 |
| 6,551,312 B2 | 4/2003 | Zhang et al. | 606/41 |
| 6,569,160 B1 | 5/2003 | Goldin et al. | 606/41 |
| 6,569,198 B1 | 5/2003 | Wilson et al. | 623/2.37 |
| 6,575,971 B2 | 6/2003 | Hauck et al. | 606/52 |
| 6,589,208 B2 | 7/2003 | Ewers et al. | 604/104 |
| 6,626,930 B1 | 9/2003 | Allen et al. | 606/213 |
| 6,632,238 B2 | 10/2003 | Ginn et al. | 606/213 |
| 6,662,034 B2 | 12/2003 | Segner et al. | 600/373 |
| 6,704,590 B2 | 3/2004 | Haldeman | 600/407 |
| 6,723,038 B1 | 4/2004 | Schroeder et al. | 600/16 |
| 6,726,716 B2 | 4/2004 | Marquez | 623/2.36 |
| 6,760,616 B2 | 7/2004 | Hoey et al. | 600/547 |
| 6,780,197 B2 | 8/2004 | Roe et al. | 606/213 |
| 6,797,001 B2 | 9/2004 | Mathis et al. | 623/2.37 |
| 6,800,090 B2 | 10/2004 | Alferness et al. | 623/2.36 |
| 6,837,886 B2 | 1/2005 | Collins et al. | 606/41 |
| 6,852,076 B2 | 2/2005 | Nikolic et al. | 600/37 |
| 6,855,143 B2 | 2/2005 | Davison et al. | 606/41 |
| 6,890,353 B2 | 5/2005 | Cohn et al. | 623/2.37 |
| 6,892,091 B1 | 5/2005 | Ben-Haim et al. | 600/509 |
| 6,899,674 B2 | 5/2005 | Viebach et al. | 600/152 |
| 6,907,297 B2 | 6/2005 | Wellman et al. | 607/122 |
| 6,908,478 B2 | 6/2005 | Alferness et al. | 623/1.11 |
| 6,913,576 B2 | 7/2005 | Bowman | 606/505 |
| 6,918,903 B2 * | 7/2005 | Bass | 604/511 |
| 6,926,669 B1 | 8/2005 | Stewart et al. | 600/439 |
| 6,942,657 B2 | 9/2005 | Sinofsky et al. | 606/15 |
| 6,949,122 B2 | 9/2005 | Adams et al. | 623/2.36 |
| 6,960,229 B2 | 11/2005 | Mathis et al. | 623/2.36 |
| 6,986,775 B2 | 1/2006 | Morales et al. | 606/139 |
| 6,989,010 B2 | 1/2006 | Francischelli et al. | 606/42 |
| 6,989,028 B2 | 1/2006 | Lashinski et al. | 623/2.37 |
| 6,994,093 B2 | 2/2006 | Murphy et al. | 128/898 |
| 6,997,951 B2 | 2/2006 | Solem et al. | 623/2.37 |
| 7,001,383 B2 | 2/2006 | Keidar | 606/41 |
| 7,025,776 B1 | 4/2006 | Houser et al. | 606/213 |
| 7,050,848 B2 | 5/2006 | Hoey et al. | 600/547 |
| 7,052,487 B2 | 5/2006 | Cohn et al. | 604/509 |
| 7,068,867 B2 | 6/2006 | Adoram et al. | 385/12 |
| 7,141,019 B2 | 11/2006 | Pearlman | |
| 7,144,363 B2 | 12/2006 | Pai et al. | 600/167 |
| 7,177,677 B2 | 2/2007 | Kaula et al. | 600/546 |
| 7,186,210 B2 | 3/2007 | Feld et al. | 600/16 |
| 7,187,964 B2 | 3/2007 | Khoury | 600/509 |
| 7,189,202 B2 | 3/2007 | Lau et al. | 600/37 |
| 7,279,007 B2 | 10/2007 | Nikolic et al. | 623/11.11 |
| 7,300,435 B2 | 11/2007 | Wham et al. | 606/34 |
| 7,303,526 B2 | 12/2007 | Sharkey et al. | 600/37 |
| 7,335,196 B2 | 2/2008 | Swanson et al. | 606/41 |
| 7,507,252 B2 | 3/2009 | Lashinski et al. | 623/2.37 |
| 2001/0003158 A1 | 6/2001 | Kensey et al. | 606/213 |
| 2001/0005787 A1 | 6/2001 | Oz et al. | 606/142 |
| 2001/0018611 A1 | 8/2001 | Solem et al. | 623/2.37 |
| 2001/0020126 A1 | 9/2001 | Swanson et al. | 600/407 |
| 2002/0002329 A1 | 1/2002 | Avitall | 600/377 |
| 2002/0016628 A1 | 2/2002 | Langberg et al. | 623/2.36 |
| 2002/0087156 A1 | 7/2002 | Maguire et al. | 606/41 |
| 2002/0087173 A1 | 7/2002 | Alferness et al. | 606/151 |
| 2002/0107478 A1 | 8/2002 | Wendlandt | 604/95.01 |
| 2002/0107511 A1 | 8/2002 | Collins et al. | 606/41 |
| 2002/0115944 A1 | 8/2002 | Mendes et al. | 600/594 |
| 2002/0169504 A1 | 11/2002 | Alferness et al. | 623/2.36 |
| 2002/0177782 A1 | 11/2002 | Penner | 600/485 |
| 2002/0183836 A1 | 12/2002 | Liddicoat et al. | 623/2.11 |
| 2002/0183841 A1 | 12/2002 | Cohn et al. | 623/2.36 |
| 2002/0188170 A1 | 12/2002 | Santamore et al. | 600/37 |
| 2003/0050685 A1 | 3/2003 | Nikolic et al. | 623/1.11 |
| 2003/0069570 A1 | 4/2003 | Witzel et al. | 606/28 |

| | | | | | | | |
|---|---|---|---|---|---|---|---|
| 2003/0069636 | A1 | 4/2003 | Solem et al. .................. 623/2.37 | 2007/0198058 | A1 | 8/2007 | Gelbart et al. ................. 606/213 |
| 2003/0078465 | A1 | 4/2003 | Pai et al. ......................... 600/16 | 2007/0213578 | A1 | 9/2007 | Khairkhahan et al. ........... 600/16 |
| 2003/0078671 | A1 | 4/2003 | Lesniak et al. ............. 623/23.64 | 2007/0213815 | A1 | 9/2007 | Khairkhahan et al. ......... 623/3.1 |
| 2003/0105384 | A1 | 6/2003 | Sharkey et al. ................. 600/16 | 2007/0249999 | A1 | 10/2007 | Sklar et al. ............... 604/101.05 |
| 2003/0105520 | A1 | 6/2003 | Alferness et al. ............. 623/2.36 | 2007/0270688 | A1 | 11/2007 | Gelbart et al. |
| 2003/0109770 | A1 | 6/2003 | Sharkey et al. ................. 600/16 | 2007/0299343 | A1* | 12/2007 | Waters .......................... 600/443 |
| 2003/0181819 | A1 | 9/2003 | Desai ............................ 600/510 | 2008/0004534 | A1 | 1/2008 | Gelbart et al. ................. 600/508 |
| 2003/0229395 | A1 | 12/2003 | Cox ............................... 623/2.36 | 2008/0004643 | A1 | 1/2008 | To et al. ........................ 606/159 |
| 2004/0002626 | A1 | 1/2004 | Feld et al. ....................... 600/37 | 2008/0004697 | A1 | 1/2008 | Lichtenstein et al. ........ 623/2.11 |
| 2004/0054279 | A1 | 3/2004 | Hanley .......................... 600/424 | 2008/0045778 | A1 | 2/2008 | Lichtenstein et al. .......... 600/16 |
| 2004/0133273 | A1 | 7/2004 | Cox ............................... 623/2.11 | 2008/0071298 | A1 | 3/2008 | Khairkhahan et al. ........ 606/151 |
| 2004/0138744 | A1 | 7/2004 | Lashinski et al. ............. 623/2.36 | 2008/0312713 | A1 | 12/2008 | Wilfley et al. ................... 607/41 |
| 2004/0153146 | A1 | 8/2004 | Lashinski et al. ............. 623/2.36 | 2009/0131930 | A1 | 5/2009 | Gelbart et al. ................... 606/41 |
| 2004/0158321 | A1 | 8/2004 | Reuter et al. .................. 623/2.36 | 2009/0157058 | A1 | 6/2009 | Ferren et al. ................. 604/891.1 |
| 2004/0176797 | A1* | 9/2004 | Opolski ........................ 606/213 | 2009/0192441 | A1 | 7/2009 | Gelbart et al. ................... 604/22 |
| 2004/0186566 | A1 | 9/2004 | Hindrichs et al. ............. 623/2.37 | 2009/0287304 | A1 | 11/2009 | Dahlgren et al. ............. 623/2.37 |
| 2004/0215232 | A1 | 10/2004 | Belhe et al. ................... 606/213 | 2011/0125172 | A1 | 5/2011 | Gelbart et al. ................. 606/159 |
| 2004/0243170 | A1 | 12/2004 | Suresh et al. .................. 606/198 | | | | |
| 2004/0249408 | A1 | 12/2004 | Murphy et al. ................ 606/198 | | | | |
| 2004/0249453 | A1 | 12/2004 | Cartledge et al. ............. 623/2.37 | | | | |
| 2004/0267358 | A1 | 12/2004 | Reitan .......................... 623/2.37 | | | | |

FOREIGN PATENT DOCUMENTS

| | | |
|---|---|---|
| WO | 03/015611 | 2/2003 |
| WO | 03/077800 | 9/2003 |
| WO | 2004/012629 | 2/2004 |
| WO | 2004/047679 | 6/2004 |
| WO | 2004/084746 | 10/2004 |
| WO | 2004/100803 | 11/2004 |
| WO | 2005/070330 | 8/2005 |
| WO | 2005/102181 | 11/2005 |
| WO | 2006/017809 | 2/2006 |
| WO | 2006/105121 | 10/2006 |
| WO | 2006/135747 | 12/2006 |
| WO | 2006/135749 | 12/2006 |
| WO | 2007/021647 | 2/2007 |
| WO | 2007/115390 | 10/2007 |
| WO | 2008/002606 | 1/2008 |
| WO | 2009/065042 | 5/2009 |

| | | | |
|---|---|---|---|
| 2005/0004668 | A1 | 1/2005 | Aklog et al. .................. 623/2.36 |
| 2005/0015109 | A1 | 1/2005 | Lichtenstein ................. 606/200 |
| 2005/0054938 | A1 | 3/2005 | Wehman et al. .............. 600/483 |
| 2005/0055089 | A1 | 3/2005 | Macoviak et al. ............. 623/2.37 |
| 2005/0060030 | A1 | 3/2005 | Lashinski et al. ............. 623/2.37 |
| 2005/0064665 | A1 | 3/2005 | Han ............................... 438/286 |
| 2005/0065420 | A1 | 3/2005 | Collins et al. ................. 600/374 |
| 2005/0065504 | A1 | 3/2005 | Melsky et al. .................. 606/16 |
| 2005/0080402 | A1 | 4/2005 | Santamore et al. ................ 606/1 |
| 2005/0096047 | A1 | 5/2005 | Haberman et al. ......... 455/432.3 |
| 2005/0096647 | A1 | 5/2005 | Steinke et al. ................... 606/41 |
| 2005/0107723 | A1 | 5/2005 | Wehman et al. .............. 600/595 |
| 2005/0107871 | A1 | 5/2005 | Realyvasquez et al. ...... 623/2.11 |
| 2005/0125030 | A1 | 6/2005 | Forsberg et al. .............. 606/213 |
| 2005/0148892 | A1 | 7/2005 | Desai ............................ 600/510 |
| 2005/0149014 | A1 | 7/2005 | Hauck et al. .................... 606/41 |
| 2005/0154252 | A1 | 7/2005 | Sharkey et al. .................. 600/37 |
| 2005/0182365 | A1 | 8/2005 | Hennemann et al. ......... 604/113 |
| 2005/0187620 | A1 | 8/2005 | Pai et al. ....................... 623/2.37 |
| 2005/0197692 | A1 | 9/2005 | Pai et al. ......................... 623/2.1 |
| 2005/0197693 | A1 | 9/2005 | Pai et al. ......................... 623/2.1 |
| 2005/0197694 | A1 | 9/2005 | Pai et al. ......................... 623/2.1 |
| 2005/0203558 | A1 | 9/2005 | Maschke ....................... 606/180 |
| 2005/0209636 | A1 | 9/2005 | Widomski et al. ............ 606/213 |
| 2005/0216054 | A1 | 9/2005 | Widomski et al. ............ 606/213 |
| 2005/0240249 | A1 | 10/2005 | Tu et al. ........................... 607/96 |
| 2005/0251116 | A1 | 11/2005 | Steinke et al. ..................... 606/8 |
| 2005/0251132 | A1 | 11/2005 | Oral et al. ........................ 606/41 |
| 2005/0256521 | A1 | 11/2005 | Kozel .............................. 606/41 |
| 2005/0267574 | A1 | 12/2005 | Cohn et al. .................... 623/2.36 |
| 2006/0009755 | A1 | 1/2006 | Sra .................................. 606/32 |
| 2006/0009756 | A1 | 1/2006 | Franischelli et al. ........... 606/32 |
| 2006/0014998 | A1 | 1/2006 | Sharkey et al. .................. 600/16 |
| 2006/0015002 | A1 | 1/2006 | Moaddeb et al. ................ 600/37 |
| 2006/0015003 | A1 | 1/2006 | Moaddes et al. ................. 600/37 |
| 2006/0015038 | A1 | 1/2006 | Weymarn-Scharli ......... 600/585 |
| 2006/0015096 | A1 | 1/2006 | Hauck et al. .................... 606/41 |
| 2006/0025800 | A1 | 2/2006 | Suresh .......................... 606/198 |
| 2006/0030881 | A1 | 2/2006 | Sharkey et al. ................ 606/213 |
| 2006/0085049 | A1 | 4/2006 | Cory et al. |
| 2006/0135968 | A1 | 6/2006 | Schaller ........................ 606/144 |
| 2006/0135970 | A1 | 6/2006 | Schaller ........................ 606/152 |
| 2006/0184242 | A1 | 8/2006 | Lichtenstein ................. 623/2.37 |
| 2006/0199995 | A1 | 9/2006 | Vijay ............................... 600/37 |
| 2006/0229491 | A1 | 10/2006 | Sharkey et al. .................. 600/37 |
| 2006/0235286 | A1* | 10/2006 | Stone et al. ................... 600/381 |
| 2006/0235314 | A1 | 10/2006 | Migliuolo et al. ............. 600/505 |
| 2006/0264980 | A1 | 11/2006 | Khairkhahan et al. ........ 606/153 |
| 2006/0281965 | A1 | 12/2006 | Khairkhahan et al. .......... 600/37 |
| 2006/0293698 | A1 | 12/2006 | Douk ............................ 606/142 |
| 2006/0293725 | A1 | 12/2006 | Rubinsky et al. |
| 2007/0016068 | A1 | 1/2007 | Grunwald et al. ............ 600/468 |
| 2007/0038208 | A1 | 2/2007 | Kefer |
| 2007/0088362 | A1 | 4/2007 | Bonutti et al. .................. 606/99 |
| 2007/0115390 | A1 | 5/2007 | Makara et al. ................ 348/552 |
| 2007/0118215 | A1 | 5/2007 | Moaddeb ...................... 623/2.37 |
| 2007/0129717 | A1 | 6/2007 | Brown, III et al. ............. 606/41 |
| 2007/0161846 | A1 | 7/2007 | Nikolic et al. .................. 600/16 |

OTHER PUBLICATIONS

Becker, R. et al., "Ablation of Atrial Fibrillation: Energy Sources and Navigation Tools: A Review," *Journal of Electrocardiology*, 37(Supplement 2004):55-62, 2004.

Buchbinder, Maurice, MD, "Dynamic Mitral Valve Annuloplasty: A Reshapable Ring for Residual and Recurring MR," from the *Foundation for Cardiovascular Medicine*, La Jolla, CA. May 24, 2007.

Calkins, Hugh, "Radiofrequency Catheter Ablation of Supraventricular Arrhythmias," *Heart*, 85:594-600, 2001.

De Ponti et al., "Non-Fluoroscopic Mapping Systems for Electrophysiology: The 'Tool or Toy' Dilemma After 10 Years," European Heart Journal 27:1134-1136, 2006.

Gelbart et al., "Automatic Atherectomy System," Office Action mailed Mar. 4, 2009 for U.S. Appl. No. 11/436,584, 7 pages.

Gelbart et al., "Automatic Atherectomy System," Amendment filed Aug. 4, 2009 for U.S. Appl. No. 11/436,584, 35 pages.

Gelbart et al., "Automatic Atherectomy System," Office Action mailed Dec. 1, 2009 for U.S. Appl. No. 11/436,584, 10 pages.

Gelbart et al., "Automatic Atherectomy System," Amendment filed Mar. 30, 2010 for U.S. Appl. No. 11/436,584, 20 pages.

Gelbart et al., "Automatic Atherectomy System," Amendment filed Oct. 25, 2010 for U.S. Appl. No. 11/436,584, 9 pages.

Gelbart et al., "Automatic Atherectomy System," Office Action mailed Dec. 14, 2010 for U.S. Appl. No. 11/436,584, 12 pages.

Gelbart et al., "Intra-Cardiac Mapping and Ablation Method," Preliminary Amendment filed Aug. 29, 2007 for U.S. Appl. No. 11/475,950, 42 pages.

Gelbart et al., "Intra-Cardiac Mapping and Ablation Method," Amendment filed Mar. 5, 2008 for U.S. Appl. No. 11/475,950, 11 pages.

Gelbart et al., "Intra-Cardiac Mapping and Ablation Method," Office Action mailed Jun. 23, 2010 for U.S. Appl. No. 11/475,950, 18 pages.

Gelbart et al., "Intra-Cardiac Mapping and Ablation Method," Amendment filed Aug. 16, 2010 for U.S. Appl. No. 11/475,950, 22 pages.

Gelbart et al., "Intra-Cardiac Mapping and Ablation Method," Office Action mailed Nov. 23, 2010 for U.S. Appl. No. 11/475,950, 25 pages.

Gelbart et al., "Intra-Cardiac Mapping and Ablation Method," Amendment filed Feb. 23, 2011 for U.S. Appl. No. 11/475,950, 28 pages.

Gelbart et al., "Medical Device for Use in Bodily Lumens, for Example an Atrium," U.S. Appl. No. 13/070,215, filed Mar. 23, 2011, 76 pages.

International Preliminary Report on Patentability, issued Jan. 6, 2009, for PCT/US2007/014902, 8 pages.

International Search Report, mailed Dec. 5, 2007, for PCT/US2007/014902, 5 pages.

International Search Report, mailed Dec. 2, 2009, for PCT/US2008/083644, 5 pages.

Konings et al., "Development of an Intravascular Impedance Catheter for Detection of Fatty Lesions in Arteries," *IEEE Transactions on Medical Imaging*, 16(4):439-446, 1997.

Lichtenstein, "Method and Apparatus for Percutaneous Reduction of Anterior-Posterior Diameter of Mitral Valve," U.S. Appl. No. 10/690,131, filed Oct. 20, 2003, 31 pages.

Mack, "New Techniques for Percutaneous Repair of the Mitral Valve," *Heart Failure Review*, 11:259-268, 2006.

Otasevic et al., "First-in-Man Implantation of Left Ventricular Partitioning Device in a Patient With Chronic Heart Failure: Twelve-Month Follow-up," *Journal of Cardiac Failure* 13(7):517-520, 2007.

Sharkey et al., "Left Ventricular Apex Occluder. Description of a Ventricular Partitioning Device," *EuroIntervention* 2:125-127, 2006.

Stiles, et al., "Simulated Characterization of Atherosclerotic Lesions in the Coronary Arteries by Measurement of Bioimpedance," *IEE Transactions on Biomedical Engineering*, 50(7):916-921, 2003.

Tanaka et al., "Artificial SMA Valve for Treatment of Urinary Incontinence: Upgrading of Valve and Introduction of Transcutaneous Transformer," *Bio-Medical Materials and Engineering* 9:97-112, 1999.

Timek et al., "Septal-Lateral Annular Cinching ('SLAC') Reduces Mitral Annular Size Without Perturbing Normal Annular Dynamics," *Journal of Heart Valve Disease* 11(1):2-10, 2002.

Timek et al., "Septal-Lateral Annular Cinching Abolishes Acute Ischemic Mitral Regurgitation," *Journal of Thoracic and Cardiovascular Surgery*, 123(5):881-888, 2002.

Valvano et al., "Thermal Conductivity and Diffusivity of Biomaterials Measured with Self-Heated Thermistors," *International Journal of Thermodynamics*, 6(3):301-311, 1985.

Written Opinion, mailed Dec. 5, 2007, for PCT/US2007/014902, 7 pages.

Written Opinion, mailed Dec. 2, 2009, for PCT/US2008/083644, 9 pages.

Gelbart et al., "Automatic Atherectomy System," Office Action mailed Jun. 15, 2011, for U.S. Appl. No. 12/950,871, 16 pages.

Gelbart et al., "Medical Device for Use in Bodily Lumens, For Example an Atrium," Office Action mailed Jul. 25, 2011 for U.S. Appl. No. 11/941,819, 9 pages.

Gelbart et al., "Automatic Atherectomy System," Amendment filed Sep. 15, 2011, for U.S. Appl. No. 12/950,871, 21 pages.

Gelbart et al., "Medical Device for Use in Bodily Lumens, For Example an Atrium," Amendment filed Nov. 23, 2011 for U.S. Appl. No. 11/941,819, 17 pages.

\* cited by examiner

LIPOSUCTION SYSTEM

FIELD OF THE INVENTION

The invention relates to the medical field and in particular to surgery and liposuction.

BACKGROUND OF THE INVENTION

The efficiency of many surgical procedures could be improved if there was a safe way to automatically stop the action of the surgical tool when it encounters an organ or type of tissue that should not be disturbed. For example, during liposuction a cannula, inserted via a minimal incision, is moved rapidly across fatty tissue in order to remove fat by using suction. Aggressive use of the cannula may result is a perforated organ and even death. On the other hand, slow movements significantly extend the duration of the surgery. A similar situation exists when using en electro-surgical tool or even an ordinary scalpel to cut in the vicinity of an organ that should not be damaged. The action of an electro-surgical tool can be stopped instantly (by stopping the current flow) if the tool could detect that it is touching or approaching a type of tissue that should not be cut. It has been known that different body tissues have different electrical properties, and the type of tissue, and even the state of the tissue can be determined from such electrical measurements. By the way of example, studies demonstrated that cancerous tissue has different electrical properties from healthy tissue. The field of tissue discrimination by electrical methods is known as "Bioimpedance Spectroscopy" and a good survey article is: "The Dielectric Properties of Biological Tissues: Literature survey" by Gabriel and Corthhout (Phys. Med. Biol. 41, 1996, pp. 2231-2249). This article is hereby incorporated by reference. Also incorporated by reference is US patent application 2007/0270688 which shares common inventors with this application. It is known that much of the information is in the way the impedance, and in particular the dielectric constant (also known as permittivity) changes with frequency. By measuring the electrical properties at multiple frequencies, typically in the range of KHz to MHz, a "signature" is derived which uniquely identifies the tissue.

In some procedures the ability to apply energy such as heat, ultrasound, microwaves, water jets and others energy sources is limited by the fear of directing the energy to the wrong organ or tissue. For example, it is known that heating up the fat during liposuction will liquefy it and make it easier to remove, but if a heated cannula is used it can cause burns to other tissues. It is desired to have a method of supplying the energy to the surgical tool as long as it is in contact with the correct tissue, instantly stopping the energy when the wrong type of tissue is touched.

Because of the relative slowness of human response time, it is desired to have the corrective action taking place automatically rather than simply alarming the surgeon. For example, when moving a cannula it is desired to instantly stop the motion of the cannula when the wrong tissue is touched, rather than sounding an alarm and relying on the response time of the surgeon.

SUMMARY OF THE DISCLOSURE

A surgical tool such as a liposuction cannula or an electro-surgical tool is equipped with a sensor at the tool tip. The sensor continuously analyzes the type of tissue in contact with the tip based on the electrical properties of the tissue. When encountering a tissue type that should not be disturbed, the action of the surgical tool is stopped. When used for liposuction, the cannula is mechanically decoupled from the handle when the wrong type of tissue is detected, thus minimizing the inertia of the part that needs to be stopped. Besides electrical sensing, other sensors can be used at the tip of the surgical tool or cannula to differentiate between tissue types. An ultrasonic transducer can discriminate tissue types based on acoustic impedance. A vibrating sensor can discriminate based on damping and other mechanical properties.

DETAILED DESCRIPTION

Figure 1:
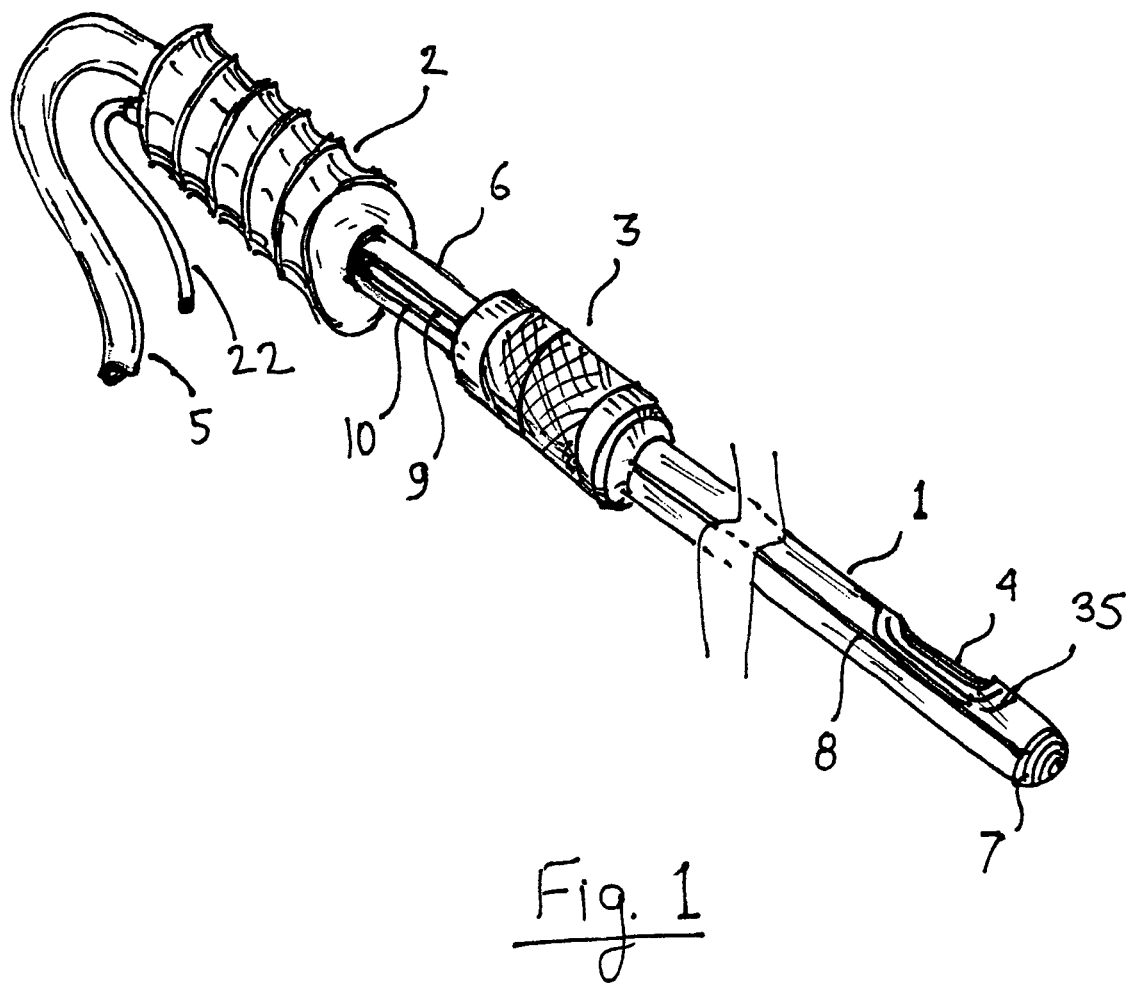
FIG. 1 is an isometric view of a liposuction tool according to the invention.

Referring to FIG. 1, a liposuction tool comprises of a cannula 1 having an opening 4 internally connected to suction hose 5. Cannula 1 is connected to handle 2 via a coupler 3 in the conventional manner. According to the invention the cannula tip is equipped with a tissue type sensor. While many sensing methods are possible, the disclosure will use, by the way of example, electrical sensing. Sensing electrode 7 is electrically insulated from cannula 1 which is typically metallic. The electrode connecting wire 8 is bonded to cannula 1 and fed through coupler 3 to conductor 9 bonded to tube 6 via insulating layer 10. Tube 6 can slide into handle 2. Electrical contact to conductor 9 is maintained by a sliding contact inside handle 2. An optional energy source 35, such as resistive heater, RF (Radio Frequency) heater or ultrasonic transducer is mounted near opening 4 and is electrically connected to handle 2 in a similar manner to electrode 7. The RF frequency can be from hundreds of KHz to several GHz, i.e. from LF to Microwave. In some applications it may be desired to replace the energy source with a mechanical or chemical action such as a rotary cutter or a high pressure liquid jet. The words "energy source" in this disclosure should be interpreted broadly as anything beyond the motion induced by the surgeon's hands. The electrical connections are brought out of handle 2 via a flexible electrical cable 22.

Figure 2:
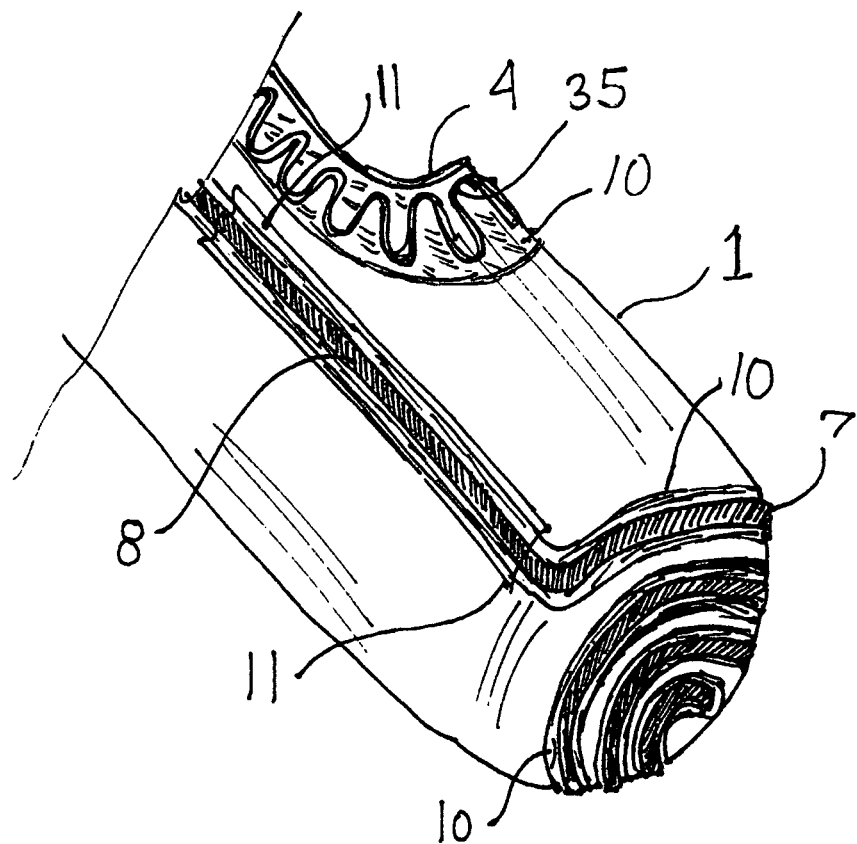
FIG. 2 is a close-up view of the tool tip showing the sensing and heating elements.
Figures 3A, 3B, 3C:
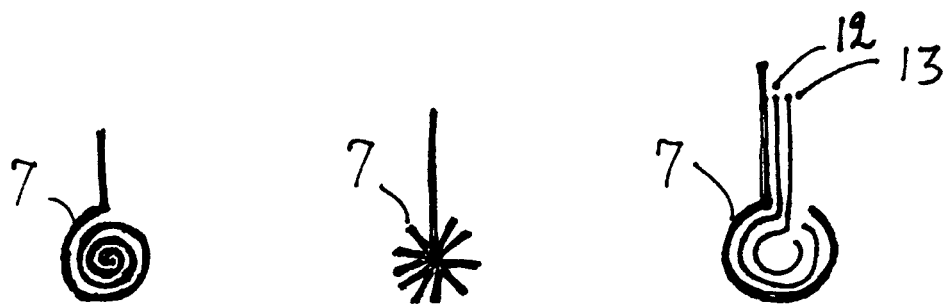
FIG. 3A is schematic view of a spiral sensing element.
FIG. 3B is a schematic view of a radial sensing element.
FIG. 3C is a schematic view of a concentric sensing electrode based on the four wire principle, having separate current injection and sensing leads.

The details of the sensing electrode are shown in FIG. 2. The metallic electrode 7 is insulated from metallic cannula 1 via a thin insulating layer 10. Electrode 7 is connected to the rest of the system via conductor 8 which is covered by a second insulating layer 11. Clearly other styles of conductors, like a miniature coaxial cable, can be used. FIGS. 3A, 3B and 3C show different styles of electrodes. FIG. 3A shows a spiral electrode similar to FIG. 2. FIG. 3B shows a radial electrode, with better performance at very high frequencies. In all three figures the return electrode is the body of the cannula, assuming it is made of metal or having a metal coated tip. FIG. 3C shows an electrode of the type known as "4 wire system". In this system the voltage sensing electrodes 12 and 13 are separate from the current injection from electrode 7 to the metallic cannula. In FIG. 3C the insulating layer does not have a gap between electrode 12 to electrode 13. The gap exposing the cannula is only on the inside of electrode 13. A four wire system is less sensitive to electrode-tissue interface problems. This type of electrodes is also known as "Kelvin Electrodes" in electrical engineering.

When energy source 35 is a heater it is desired to use a very thin foil (preferably 5 micron to 100 micron) on top of an electrically and thermally insulating layer 10. This allows turning the heater off instantly when the sensing electrode 7 detects a tissue that should not be affected. Typical choices for insulating layer 10 and cover layer 11 are polyimide or ceramics. A ceramic coating such as alumina or zirconia can be applied by plasma spraying.

Figure 4:
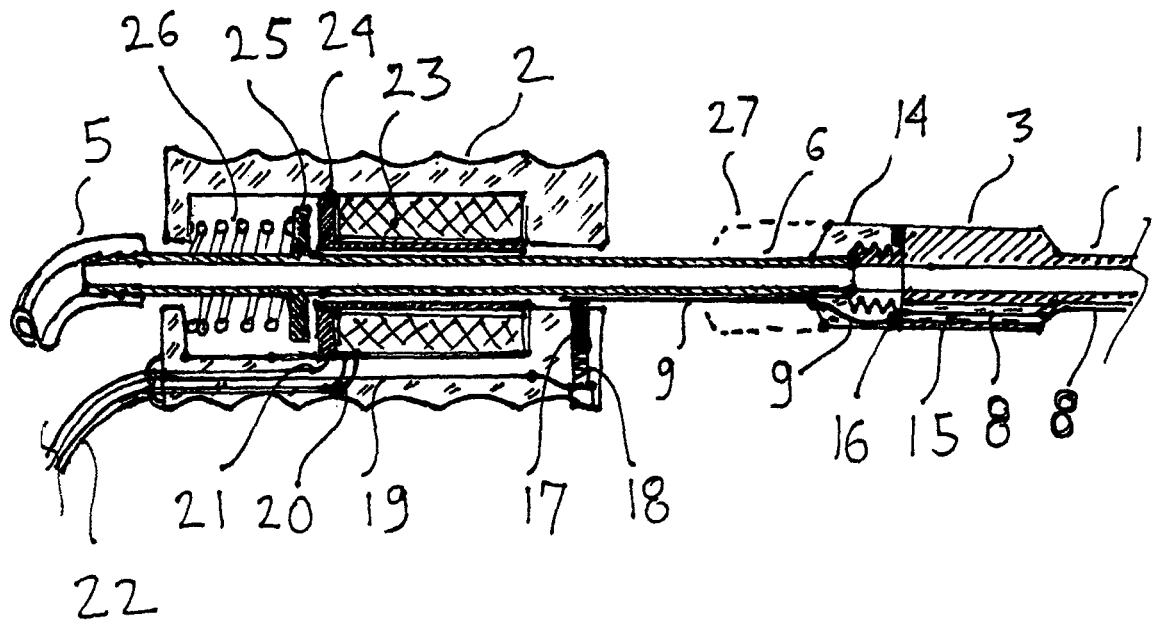
FIG. 4 is a longitudinal cross section of the liposuction cannula and handle.

In order to stop the action of the cannula instantly and prevent the perforation of an internal organ when detected by the sensing electrode 7, the cannula can be instantly decoupled from the handle as shown in FIG. 4. The cannula 1 is connected to handle 2 via a coupler 3 in the conventional manner. The mating part 14 is mounted on tube 6 that can slide through handle 2 to the position shown by dotted line 27. A ferromagnetic ring 25 is attached to tube 6 and is held in place by solenoid coil 23 having a ferromagnetic face 24. It is important to have the mating faces of 24 and 25 highly accurate and smooth in order to minimize the power required by coil 23. By the way of example, only about 2 W is needed to hold tube 6 with a force of 10 Nt when mating faces are accurate. When the system detects the presence of the wrong tissue the current through coil 23 is stopped, causing the handle to slide over tube 6 and preventing the cannula from perforating the organ touched by the tip. An extra feature of the design is that the cannula will decouple when an excessive force is used, as the holding force of coil 23 can be adjusted by the current through it. When the cannula is retracted slightly and no longer touches the wrong tissue, spring 26 will bring parts 24 and 25 together and the magnetic force will keep them together till the next instance of touching the wrong tissue. This mode of automatic reset is very compatible with the rapid forward and backward motion imparted to handle 2 by the surgeon during liposuction. Electrical conductor 8 is fed via coupler 3 via an insulated bore 15. The mating part 14 is made of insulating material and has a conductive ring 16 that makes electrical contact between conductor 9 and conductor 8. Conductor 9 is not covered by a top insulating layer, in order to have a sliding contact with carbon brush 17 and spring 18 (similar to electrical brushes in a DC motor). Wire 19 coming from external flexible cable 22 completes the circuit. Cable 22 also carries the return wire 21 (typically forming a coaxial cable with wire 19) as well as the leads 20 for powering coil 23.

Figure 5A:
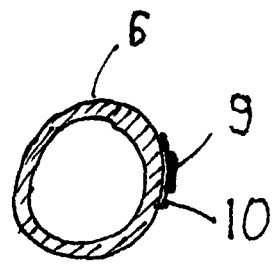
FIG. 5A is a cross section of the cannula in areas the electrical conductor is exposed.
Figure 5B:
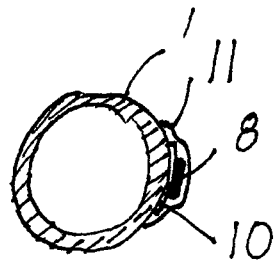
FIG. 5B is a cross section of the cannula in areas the electrical conductor is insulated.

FIG. 5A shows the cross section of the cannula in part 6 and FIG. 5B shows the cross section of the main cannula body, where conductor 8 is insulated from cannula by insulator 10 and covered by insulator 11. Both conductor 8 and insulating layers 10 and 11 can be very thin, preferably 5 to 100 microns.

The principle of distinguishing between tissue types is based on bioimpedance spectroscopy (i.e. measuring tissue impedance at different frequency). A simple resistance measurement is not sufficient because of the large variability in resistance. By measuring both the real and imaginary (capacitive) component of the electrical impedance the tissue touched by sensing electrodes 7 can be identified. In liposuction, the tissue has to be matches to one of the following three categories: fat, blood (and saline solution which is electrically very similar to blood) and "other tissue" such as muscle, dermis, blood vessels, internal organs etc. Touching "other tissue" should cause the cannula to disengage or, if preferred, generate a warning signal such as a light coming on, or both. The saline solution is injected during the procedure and is very similar to blood. There is no need to distinguish it from blood.

Figure 6:
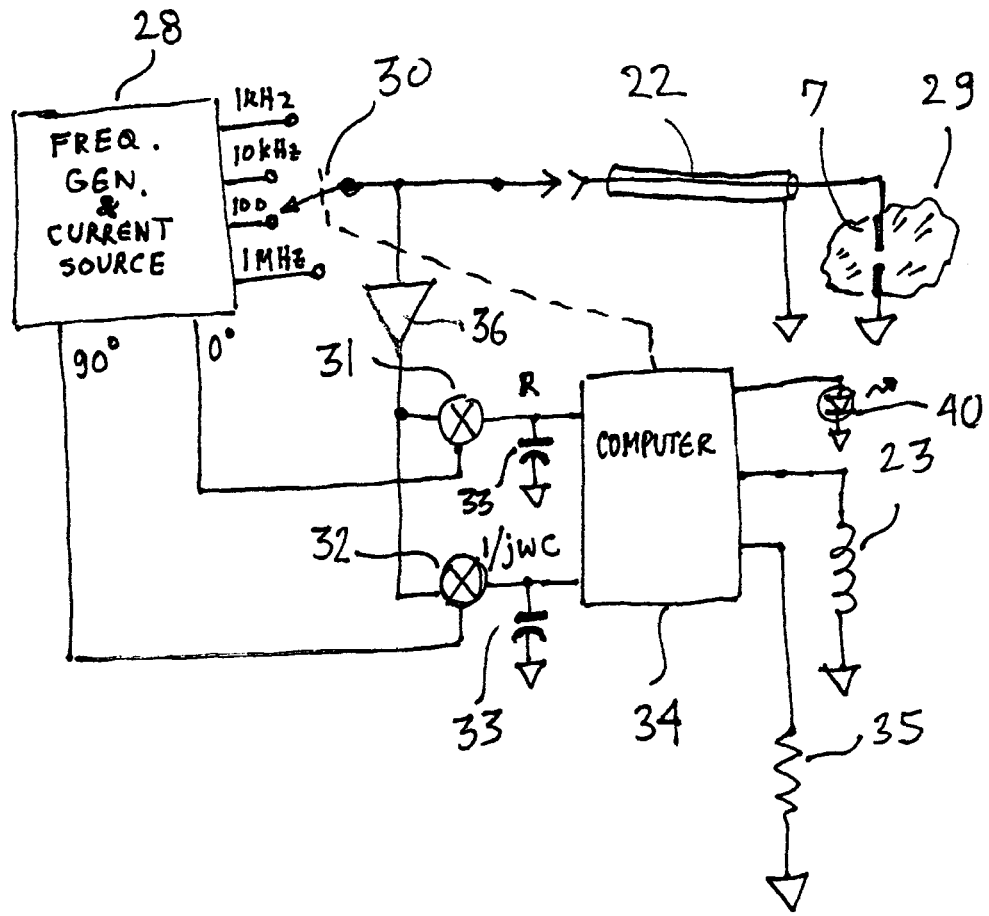
FIG. 6 is a schematic diagram of the electrical circuit used to identify the type of tissue.

Fat is characterized by a high resistance and a high dielectric constant (also referred to as "permittivity") dropping off rapidly above a few KHz. Blood and saline are characterized by a low resistance and a high dielectric constant staying high up to several MHz. All other tissues have a medium resistance and a dielectric constant gradually dropping off. Specific patterns can be stored in the system to recognize specific types of tissues. For example, cancerous tissue has a different bioimpedance signature than normal tissue and this can be used to remove it without damaging normal tissue. By using several frequencies, such as 1 KHz, 10 KHz, 100 KHz and 1 MHz a clear signature can be generated. There is little information in frequencies below 100 Hz and over 10 MHz. The art of measuring bioimpedance is well known and a typical circuit is shown in FIG. 6. A current source 28 can be switched by an electronic switch 30 to generate the required frequencies. This is typically implemented by a single IC digital frequency synthesizer. The synthesizer is connected as a current source to sensing electrode 7 in contact with tissue 29. The impedances measured depend on the size of electrodes 7 but for a typical liposuction cannula were found to be in the range of 20 Ohms to 2000 Ohms. The impedance is separated into the resistive and capacitive components by multipliers (or mixers) 31, 32 multiplying the sensed signal by the sine and cosine outputs of the 28 (i.e. by two outputs shifted by 90 degrees). Amplifier 36 is used to buffer the signal and can be placed closer to electrode 7 for better performance (also known as "active probe"). Capacitors 33 filter out the high frequency component. Computer 34 compares the resistive and capacitive components to pre-programmed patterns to identify tissue type. The analog voltages are interfaced to computer 34 via analog to digital converters (not shown), unless the computer IC has a built-in analog to digital converter. After classification of tissue type computer 34 stops the current through coil 23 whenever it senses tissue other than blood or fat or by any other pre-programmed criterion. It can also control warning light 40 or any other form of warning as well as control energy source 35. The details of such electronic circuits are well known in the art.

Figure 7:
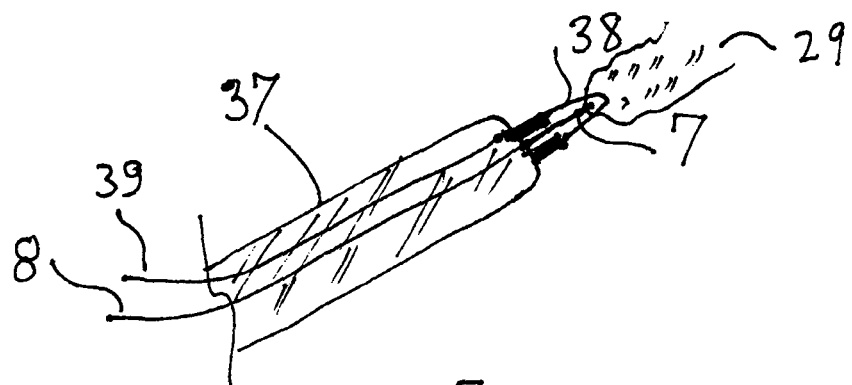
FIG. 7 is a schematic view of an electro-surgical tool with an added sensing electrode according to the invention.

A similar system can be used to control other surgical tools such as electro-surgical instruments. These well known tools use RF energy to cut tissue by ablation. They are preferred to scalpels for many procedures because of reduced bleeding. FIG. 7 shows a tool 37 connected to an RF source (not shown) by wire 37. The RF energy is fed to cutting tip 38 and forms a path between tip 38, typically a U-shaped wire, and the body of the patient. A sensing electrode 7 is added to the standard tool. Since the RF is typically pulsed, the gaps between pulses can be used to ground tip 38 and sense type of tissue 29 by measuring the impedance between electrode 7 and temporarily grounded tip 38 in a similar manner to the system discussed earlier. When a tissue type that should not be cut is detected, RF energy to tip is stopped. Without RF energy the blunt tip 38 can not cut. For tools using continuous RF energy, the RF signal can be paused many times a second for a few milliseconds each time. This allows electrical measurements with very little affect on the operation of the tool. The same concept can be adapted to many other surgical tools. In this disclosure the term "surgical tool" should be interpreted broadly as any tool inserted into the body, regardless of shape or function.

While the preferred embodiment describes the use of an electrical sensor at the tip of the surgical tool, it should be understood that the invention covers all methods of sensing. It is well known that there is a difference between the acoustic and mechanical properties of different tissues. If electrode 7 in FIG. 2 is replaced by a thin ultrasonic transducer, the type of tissue can de established by the echo similar to the well known IVUS (Intravascular Ultrasound) system used inside arteries. Sometimes a mechanical transducer operating at a relatively low frequency (Hz to KHz range) can be used to measure stiffness and damping. Such a transducer can be piezoelectric or electromagnetic. In this disclosure the term "sensor" should be interpreted as any sensing method.

Most sensors not only sense the immediate layer they contact but "see" some depth into the tissue. In the case of an electrical sensor this depth is approximately equal to the electrode spacing. Ultrasonic sensors can see a great depth into the tissue. This can be used to stop the action of the tool before it reaches the tissue that should not be disturbed. By setting the trip point of the system, a programmable thickness of removable tissue can be left in place. Similarly the response time of the system can be programmed in order to reduce nuisance tripping by a very brief contact or brief transition between tissue types. It is desired that these parameters can be set by the surgeon, as the preference may vary between surgeons.

The invention claimed is:

1. A tissue removal system comprising:
   a suction source;
   a cannula, comprising an opening arranged to be inserted into a body, the cannula further comprising a lumen, the lumen providing at least a portion of path between the opening and the suction source along which tissue from within the body is removed;
   a handle for use by an operator to manipulate at least the portion of the cannula comprising the opening, the opening positioned in the body, the manipulating of at least the portion of the cannula comprising the opening comprising at least an advancing and retracting movement of at least the portion of the cannula comprising the opening;
   a coupler to displaceably couple the handle to the cannula, the handle selectively displaceable between a first configuration in which the coupler couples the handle to the cannula with a coupling force sufficient to allow the manipulating of at least the portion of the cannula comprising the opening, the opening positioned in the body, and a second configuration in which the coupler displaceably couples the handle to the cannula with a coupling force sufficient to interrupt the manipulating of at least the portion of the cannula comprising the opening, opening positioned in the body;
   at least one sensor; and
   a system communicatively coupled to the at least one sensor to receive a signal therefrom, the signal indicative of at least one physical characteristic of tissue within the body to which at least the portion of the cannula comprising the opening is positioned at least proximate at least during manipulation of at least the portion of the cannula comprising the opening, the opening positioned in the body, the system configured to discriminate between at least a first tissue type and a second tissue type based on the at least one physical tissue characteristic indicated by the signal received from the at least one sensor, the system communicatively coupled to the coupler and configured to provide control information, the control information correlating the first configuration and the second configuration to a respective one of the first tissue type and the second tissue type that is discriminated by the system based at least on the at least one physical tissue characteristic indicated by the signals received from the at least one sensor.

2. The tissue removal system of claim 1 wherein the system-is configured to cause the coupler to automatically switch between the first configuration and the second configuration based at least on the discrimination between the first tissue type and the second tissue type.

3. The tissue removal system of claim 1 wherein the at least one physical tissue characteristic comprises a tissue electrical property.

4. The tissue removal system of claim 1 wherein the at least one physical tissue characteristic comprises a tissue electrical impedance.

5. The tissue removal system of claim 1 wherein the at least one physical tissue characteristic comprises a tissue electrical impedance as measured over multiple frequencies.

6. The tissue removal system of claim 1, further comprising an energy source, the energy source controllable to selectively provide energy within the body to liquefy fatty tissue.

7. The tissue removal system of claim 6 wherein the system is configured to control the energy source to selectively provide energy within the body to liquefy fatty tissue based at least on the discrimination between the at the first tissue type and the second tissue type.

8. The tissue removal system of claim 6 wherein the energy source comprises an RF energy source.

9. The tissue removal system of claim 6 wherein the energy source comprises an ultrasound energy source.

10. The tissue removal system of claim 1 further comprising an electrical heating element physically coupled to the cannula, the electrical heating element positionable within the body to selectively liquefy fatty tissue therein.

11. The tissue removal system of claim 1 wherein the coupler comprises an electromagnetic coupling.

12. The tissue removal system of claim 1 wherein the handle is coupled to the cannula at a first position along the cannula when the coupler is in the first configuration, and wherein the handle is arranged to slide along the cannula away from the first position when the coupler is in the second configuration.

13. The tissue removal system of claim 12 wherein the device further comprises a spring arranged to provide a biasing force directed to oppose the sliding of the handle along the cannula away from the first position when the coupler is in the second configuration.

14. A selective tissue removal system, comprising:
   a cannula, including an opening fluidly connected to a suction source via a lumen;
   a sensor carried by the cannula, the sensor responsive to a tissue characteristic when proximate a tissue;
   a computing device coupled to the sensor and which discriminates between a first tissue type and a second tissue type based on the tissue characteristic detected by the sensor; and
   a handle slideably connected to the cannula,
   the handle controllable by the computing device between a first configuration in which the handle fixedly couples to the cannula to permit free manipulation of the cannula opening when positioned within a body when the first tissue type is detected, and a second configuration in which the handle slideably decouples from the cannula to limit manipulation of the cannula opening within the body when the second tissue type is detected.

15. The system of claim 14, further comprising an electromagnet disposed at least partially within the handle and a magnetic material rigidly affixed to the cannula.

16. The system of claim 15 wherein the magnetic material is rigidly affixed to an exterior surface of the cannula.

17. The system of claim 15 wherein the computing device is controllingly coupled to the electromagnet.

18. The system of claim 17 wherein the computing device energizes the electromagnet to fixedly couple the cannula to the handle via the magnetic material in the first configuration; and wherein computing device de-energizes the electromagnet to slideably decouple the handle from the cannula via the magnetic material in the second configuration.

19. The system of claim 14 wherein the tissue characteristic comprises a tissue electrical property.

20. The system of claim 14 wherein the tissue characteristic comprises a tissue electrical impedance.

21. The system of claim 14 wherein the tissue characteristic comprises a tissue electrical impedance as measured over multiple frequencies.

22. The system of claim 14, further comprising an energy source, the energy source controllable to selectively provide energy within the body to liquefy fatty tissue.

23. The system of claim 22 wherein the computing device is configured to control the energy source to selectively provide energy within the body to liquefy fatty tissue based at least on the discrimination between the first tissue type and the second tissue type.

\* \* \* \* \*

UNITED STATES PATENT AND TRADEMARK OFFICE
CERTIFICATE OF CORRECTION

PATENT NO.        : 8,489,172 B2
APPLICATION NO.   : 12/010458
DATED             : July 16, 2013
INVENTOR(S)       : Daniel Gelbart et al.

It is certified that error appears in the above-identified patent and that said Letters Patent is hereby corrected as shown below:

In the Claims

Column 6, Lines 9-10:
"2. The tissue removal system of claim 1 wherein the system-is configured to cause the coupler to automatically" should read, --2. The tissue removal system of claim 1 wherein the system is configured to cause the coupler to automatically--.

Column 6, Line 29:
"least on the discrimination between the at the first tissue type" should read, --least on the discrimination between the first tissue type--.

Signed and Sealed this
Eleventh Day of February, 2014

Michelle K. Lee
*Deputy Director of the United States Patent and Trademark Office*